United States Patent [19]

Sato et al.

[11] Patent Number: 4,812,310

[45] Date of Patent: Mar. 14, 1989

[54] PRESERVING SOLUTION FOR BLOOD OR PACKED BLOOD CELLS AND METHOD FOR PRESERVING BLOOD OR PACKED BLOOD CELLS BY USING THE SAME

[75] Inventors: Toru Sato, 2560, Hatagasaki, Yonago-shi, Tottori-ken; Naoto Okazaki, Yonago; Katsumi Hiyoshi, Hamada, all of Japan

[73] Assignee: Toru Sato, Yonago, Japan

[21] Appl. No.: 88,450

[22] Filed: Aug. 24, 1987

[30] Foreign Application Priority Data

Aug. 29, 1986 [JP]  Japan .................. 61-204269

[51] Int. Cl.$^4$ .................. A61K 35/14; A01N 1/02
[52] U.S. Cl. .................. 424/101; 435/2
[58] Field of Search .................. 435/2; 424/101

[56] References Cited

U.S. PATENT DOCUMENTS

| | | | |
|---|---|---|---|
| 3,874,384 | 4/1975 | Deindoerfer et al. | 424/101 |
| 4,473,552 | 9/1984 | Jost | 435/2 |
| 4,585,735 | 4/1986 | Meryman et al. | 424/101 |
| 4,704,352 | 11/1987 | Miripol et al. | 435/2 |

FOREIGN PATENT DOCUMENTS 59-137064  8/1984  Japan .
60-168464  8/1985  Japan .
61-25558   2/1986  Japan .

OTHER PUBLICATIONS

Journal of Japan Society of Blood Transfusion, vol. 32, No. 1, pp. 148 to 150.

Journal of Japan Society of Blood Transfusion, vol. 32, No. 2, p. 313.

*Primary Examiner*—Sam Rosen
*Attorney, Agent, or Firm*—Armstrong, Nikaido, Marmelstein & Kubovcik

[57] ABSTRACT

A preserving solution for blood or packed blood cells comprising an anticoagulant solution containing citric acid, sodium citrate and glucose; an effective amount of glycerin; and an effective amount of mannitol. The use of the blood preserving solution makes it possible to preserve blood at a low temperature of from the freezing temperature of plasma (about $-1°$ C.) to $3°$ C. and to extend the period of preservation to 4 or 5 weeks without any further special additives.

10 Claims, 4 Drawing Sheets

PRESERVING SOLUTION FOR BLOOD OR PACKED BLOOD CELLS AND METHOD FOR PRESERVING BLOOD OR PACKED BLOOD CELLS BY USING THE SAME

BACKGROUND OF THE INVENTION

The present invention relates to a preserving solution for blood or packed blood cells (hereinafter generically referred to as "blood", unless otherwise noted) for transfusion and a method for preserving blood by using the preserving solution.

Heretofore, blood for transfusion was taken into a sterilized sealed container in which a preserving solution containing an anticoagulant and glucose was placed and preserved at low temperatures within the range of 4° to 6° C. (5° C. on the average) in a refrigerator.

The most common blood preserving method which was utilized in many countries was a method wherein CPD solution, which had a formula wherein a phosphate was added to ACD solution being an original anticoagulant solution, was used as a preserving solution, and blood mixed with CPD solution was preserved at 4° to 6° C. The reason why this method was widely used was that there were may papers reporting that CPD solution which had the formula wherein a phosphate was added to ACD solution had a stronger buffer effect against pH change due to the presence of the phosphate, as compared to ACD solution which contained citric acid, citrate and glucose, and accordingly the functions of erythrocytes preserved could be maintained at a higher level.

Further, in order to prevent the lowering of the functions of erythrocytes during preservation which could not be prevented by using CPD solution, there was proposed a method using a preserving solution wherein a substance such as inosine, adenine or adenosine was added to CPD solution. Such preserving solutions wherein adenine was added to CPD solution were generally used in the United States of America and other countries. However, it is said that this method is less than perfect, from the standpoint that there is a possibility that a surplus of the additive such as adenine, or hypoxanthine which is a metabolite of the additive causes an adverse effect after the preserved blood is transfused into a human body.

Moreover, cells have Na—K pump by which the concentrations of electrolytes in the inside and outside of each cell are controlled. Hemocytes including erythrocytes also have the Na—K pump. It is well known that when blood is preserved at low temperatures, the function of the pump is lowered, which causes the following phenomena: With respcet to $Na^+$ which is present in a large quantity in plasma among the electrolytes in blood, the concentration of $Na^+$ in plasma is gradually lowered during storage. With respect to $K^+$ which is present in a small quantity in plasma, the concentration of $K^+$ in plasma is gradually increased due to exudation of $K^+$ from hemocytes. Further, it is well known that hemolysis occurs with prolonged period of preservation, which results in an increase in the amount of free hemoglobin. The above-mentioned phenomena cause serious clinical problems. Nevertheless, there has not been made any improvement with respect to the phenomena up to date.

With respect to the blood preserving temperature, Parpart reported, in 1947, a study wherein blood was preserved at temperatures over the range of 0° to 15° C. The report described that while preservation at a low temperature was preferable to maintain the function of erythrocytes, preservation at a temperature higher than the preserving temperature (4° to 6° C.) adopted at present was preferable to prevent changes of the concentrations of electrolytes including the decrease in the amount of $Na^+$ and the increase in the amount of $K^+$ in plasma, and hemolysis during preservation. The preserving temperature (4° to 6° C.) adopted at present was determined by taking into consideration the knowledges obtained from the report and a fluctuation in the temperature control of a refrigerator at that time, and further from the standpoint of surely avoiding damages resulting from freezing.

However, the manufacturing technique of refrigerators has been greatly advanced since then and the presently available refrigerators have been significantly improved in performance. Uda et al reported that any remarkable hemolysis did not occur even when the preserving temperature was lowered to −1° C. during still longer storage condition for six weeks (at the 33rd Congress of Japan Society of Blood Transfusion, June, 1985, in Sendai, Japan).

Even though the allowable period of preservation can be extended by the method of lowering the preservation temperature so as to slow down the metabolism of erythrocytes, it was found that the above-mentioned decrease in $Na^+$ concentration and increase in $K^+$ concentration could not be suppressed. Moreover, it was reported by Nishikawa et al that the low-temperature preservation tended to increase hemolysis as compared to the conventional preservation at 4° to 6° C. (at the 34th Congress of Japan Society of Blood Transfusion, June, 1986, in Nagoya, Japan).

There is a freezing-preservation method wherein erythrocytes are completely frozen as a blood preservation method which has given actual results other than the above-mentioned methods. This method is suitable for a long-term preservation wherein a unit of preservation time is year, because the functions of erythrocytes are not damaged through storage. It is necessary to add large quantities of chemicals such as glycerin to blood as a cryoprotective agent. When the preserved blood is thawed without removing the glycerin added in a large quantity, the blood is readily hemolyzed. Therefore, it is essential to quickly remove cryoprotective agents such as glycerin added in a large amount before transfusion of such frozen and thawed blood. The work requires a great deal of labor and time and also special device and container, which results in increase in cost. Therefore, the freezing method has been used mainly to preserve a rare type of blood and has not spread as a general blood preserving method.

It is an object of the present invention to provide a preserving solution for blood which is capable of suppressing the decrease in $Na^+$ concentration and the increase in $K^+$ concentration in plasma and the increase in amount of free hemoglobin caused by hemolysis, whereby a preservation at a temperature lower than the conventional preserving temperature is made possible.

Another object of the present invention is to provide a method for preserving blood whereby the lowering of the functions of erythrocytes are suppressed while reducing hemolysis to a lower level, which enables a prolonged preservation of blood.

These and other objects of the present invention will become apparent from the description hereinafter.

SUMMARY OF THE INVENTION

The present invention provides a blood preserving solution comprising an anticoagulant solution containing citric acid, sodium citrate and glucose; and an effective amount of glycerin and an effective amount of mannitol.

The present invention further provides a method for preserving blood which comprises adding, to blood, a blood preserving solution comprising an anticoagulant solution containing citric acid, sodium citrate and glucose; and an effective amount of glycerin and an effective amount of mannitol, and preserving the blood at a low temperature equal to or higher than the freezing temperature of plasma.

DETAILED DESCRIPTION

Figure 1:
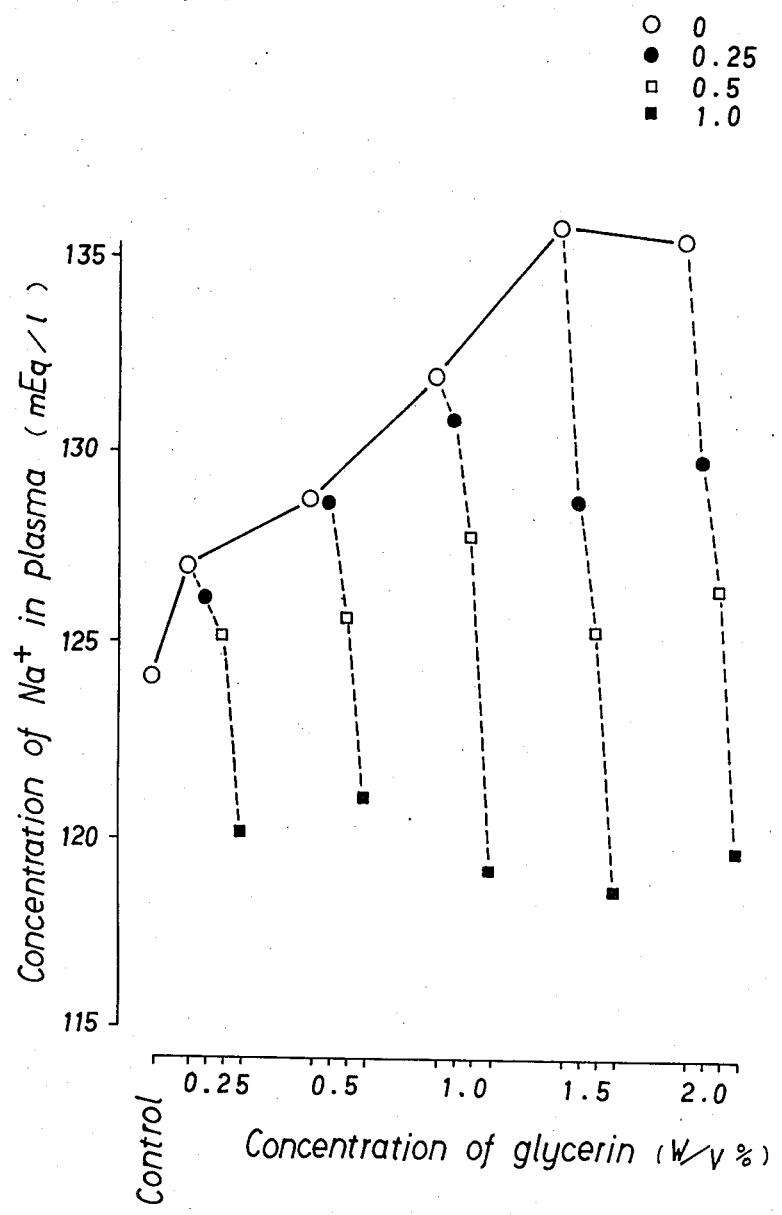
FIG. 1, FIG. 2, FIG. 3 and FIG. 4 are graphs showing the effects of the amounts of glycerin and mannitol added on the concentration of plasma $Na^+$, the concentration of plasma $K^+$, the concentration of free hemoglobin and the hemolysis rate in preservation of blood, respectively.
Figure 2:
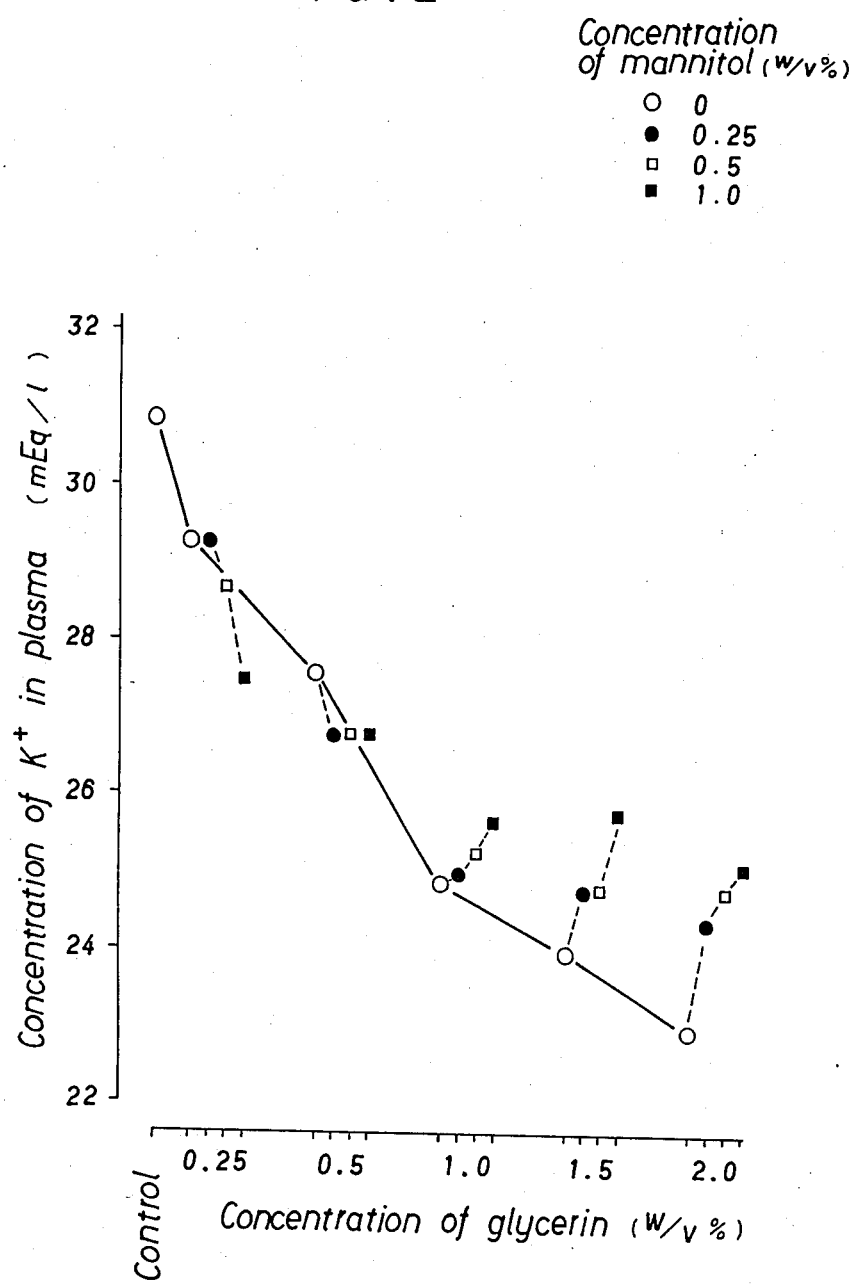
Figure 3:
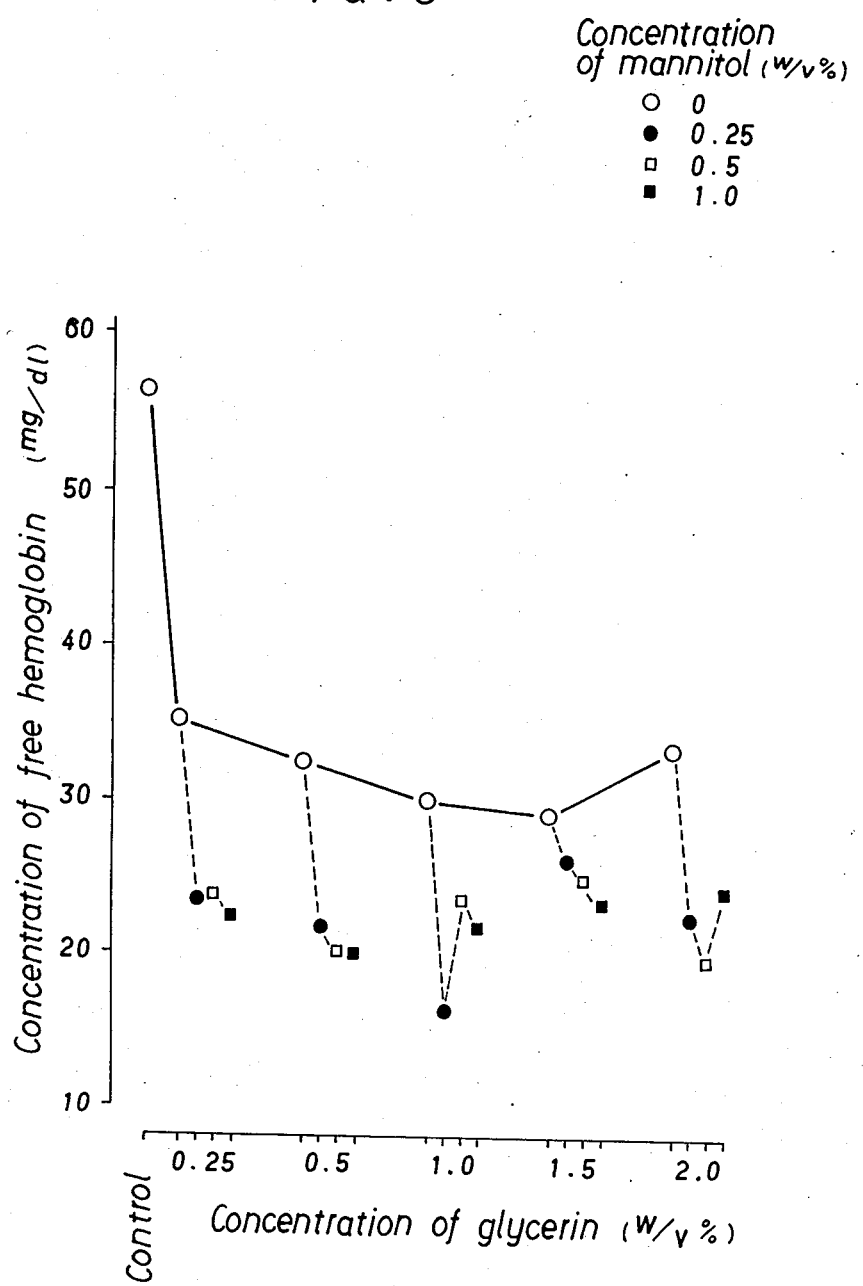
Figure 4:
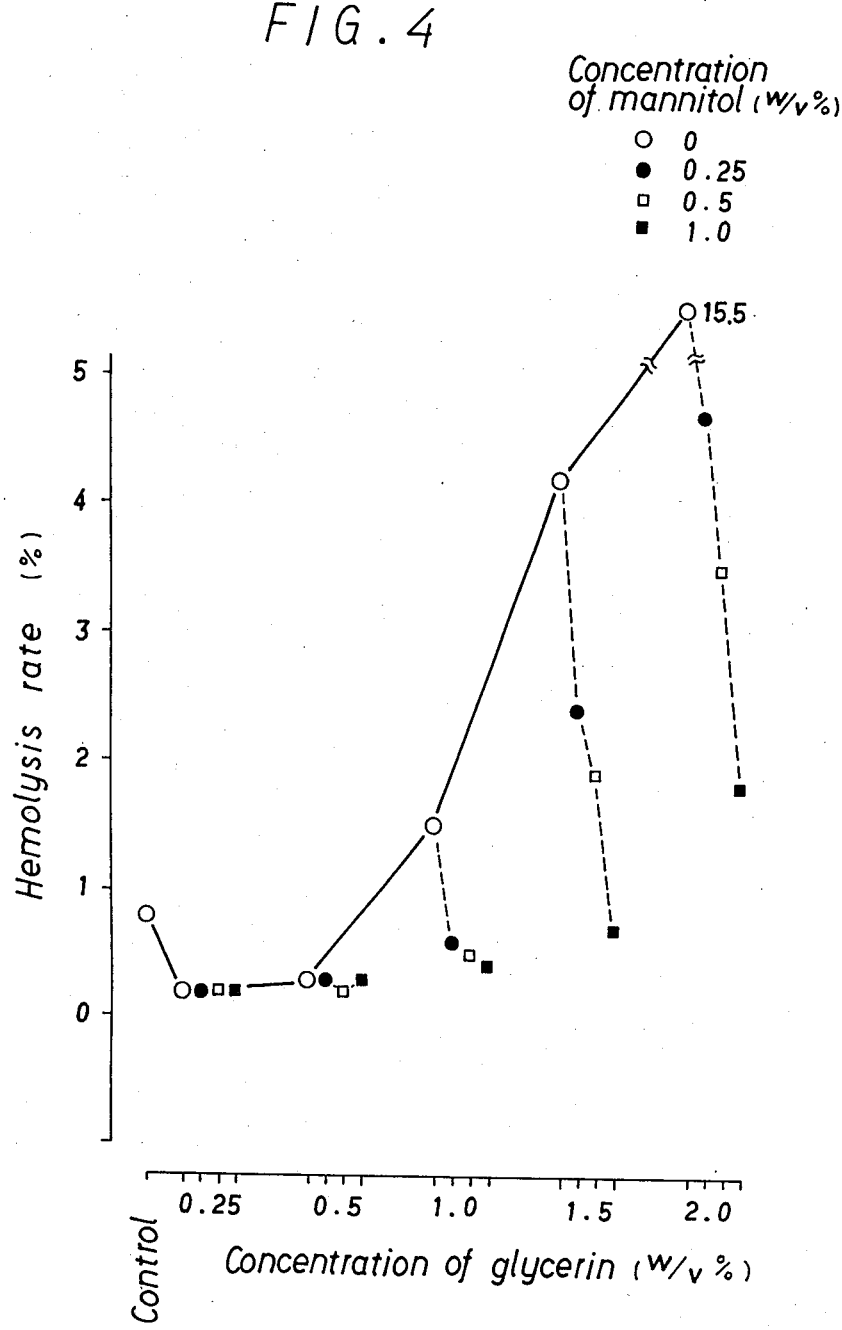

A decrease in the oxygen transport function of erythrocytes during preservation is caused by worsening of the metabolic environment of blood which results from a lowering of pH of blood with acidic substances, such as carbon dioxide, produced by metabolism of blood.

The present inventors found previously that the oxygen transport function of erythrocytes could be maintained favorably by using a gas-permeable container as a blood preservation container so as to reduce the lowering of pH of blood by removing the produced and accumulated carbon dioxide by spontaneous diffusion.

On the basis of this finding, the present inventors determined the $CO_2$ permeability of a blood preservation container which was optimal for the preservation of blood and filed patent applications directed to a blood preserving method using such gas-permeable container (Japanese Unexamined Patent Publication Nos. 59-137064, 60-168464, and 61-25558).

Further, it was found that when blood was preserved in the above-mentioned gas-permeable container at 0° to 2° C. (1° C. on the average), which temperature was lower than the conventional preserving temperature, the effect of the gas-permeable container with respect to maintenance of erythrocyte functions was significantly enhanced.

However, it was found that phenomena such as imbalance of electrolyte concentrations between the inside and outside of red blood cells and the fragility of red blood cells against the osmotic pressure could not be avoided by the method and the preservation using the conventional preserving solution at such lower temperature was undesirable.

In order to solve this problem, the present inventors have had an idea of utilizing glycerin which is used in a depression treatment for cerebral edema to depress the change of the electrolyte concentrations during preservation. However, the effect of glycerin reaches the peak in a concentration in the vicinity of 1.5 w/v %, and any better effect cannot be expected when the concentration of glycerin is increased more than the above value. The reason therefor is estimated as follows: There are two or more mechanisms for maintaining the electrolyte concentrations to keep the electrolyte balance between the inside and outside of red blood cells. Glycerin acts on the one of these mechanisms.

Further, when blood to which glycerin is added is preserved, the glycerin concentrations in the inside and outside of blood cells are equilibrated during preservation, because glycerin can pass freely through the cell membrane. When the blood is transfused into a human body, the glycerin present outside the blood cells of the transfused blood is rapidly diluted with blood of the human body so that the concentration of glycerin decreases, while some time is required in migration of the glycerin present inside the blood cells of the transfused blood to the outside thereof. As a result, a state wherein the glycerin concentrations in the inside and the outside of the blood cells are different from each other occurs temporarily. By the glycerin concentration difference, the water present outside the blood cells is introduced into the inside of the blood cell, whereby the blood cells are swollen and finally broken, namely hemolysis occurs.

The present inventors have found that when mannitol which is clinically used in a depression treatment for cerebral edema and which does not pass throuth the cell membrane is added together with glycerin to blood, some portion of the water present inside the blood cells is forced to pass outside the cell during preservation, whereby the swelling of the blood cell which occurs after transfusion of the blood into a living body can be reduced to a minimum.

As described above, by adding some mannitol to blood, the swelling of blood cells can be prevented during the preservation and after transfusion to a living body, which results in the suppression of hemolysis. However, the addition of mannitol in a large quantity causes a remarkable transudation of electrolytes which is suppressed with glycerin. Accordingly, the ratio of glycerin to mannitol is important.

It has been found that, by adding glycerin and mannitol to a conventional preserving solution such as ACD solution or CPD solution, respectively, so that the concentration of glycerin is 0.5 to 1.5 w/v % and the concentration of mannitol is 0.1 to 1.0 w/v %, on the basis of the amount of blood to be preserved, the decrease in $Na^+$ concentration and the increase in $K^+$ concentration in the plasma and the hemolysis can be prevented, and as a result, blood can be preserved at a temperature lower than the conventional preserving temperature, i.e. from 4° to 6° C.

On the other hand, it is known that the preservation of blood causes the lowering of the activity of a key enzyme which controls the metabolism of erythrocytes, so that the metabolism of erythrocytes is retarded. Glycerin is an intermediate metabolite of the glycolysis pathway which is present in reaction systems subsequent to the reaction which undergoes the effect of the key enzyme. Further glycerin is a substance consumed in a reaction system which supplies reduction-type coenzymes which are few among coenzymes obtained in the glycolysis pathway. From this point of view, the effect of glycerin on the reduction of the metabolic function of blood preserved can be expected.

Further, it has been found that when blood to which CPD solution is added is preserved in a gas-permeable container at 0° to 2° C. (1° C. on the average), the functions of erythrocytes can be maintained at a significantly high level and the period of preservation can be extended. Moreover, it has been found that when blood to which small amounts of glycerin and mannitol are added together with CPD solution is preserved, the changes of the electrolyte concentrations are suppressed, the hemolysis is prevented and the resistance of red blood cell against osmotic pressure is increased.

The present invention has been completed on the basis of the above-mentioned findings.

The present invention will be explained in detail hereinafter.

The blood preserving solution of the present invention is a solution prepared by adding glycerin and mannitol to a conventional blood preserving solution containing citric acid, sodium citrate and glucose, such as ACD solution or CPD solution, so as to suppress the decrease in $Na^+$ concentration and the increase in $K^+$ concentration in plasma and the hemolysis which are phenomena occurring during the preservation of blood.

It is preferable that glycerin and mannitol are added so that the concentration of glycerin is 0.5 to 1.5 w/v % and the concentration of mannitol is 0.1 to 1.0 w/v %, especially 0.1 to 0.5 w/v %, on the basis of the amount of blood to be preserved. When the concentration of glycerin is lower than the above range, the effect of glycerin is not exhibited. The effect of glycerin reaches the peak in a concentration of about 1.5 w/v % on the basis of the amount of blood to be preserved and in a concentration higher than the above value, the effect of glycerin is not enhanced any more and the electrolyte concentration equilibrium tends to be destroyed. When the concentration of mannitol is higher than the above range, the change of the electrolyte concentration inside and outside the blood cells, which is suppressed by the addition of glycerin, again becomes remarkable. The addition of mannitol in a concentration lower than the above range is almost ineffective.

In order to preserve blood more satisfactorily, it is preferable to add a material serving as an energic source for metabolism of blood cells, for example, sodium phosphate, and/or a material for maintaining the functions of erythrocytes which decrease with increasing preservation period, for example, adenine, adenosine and inosine.

By taking, as an example, the case of using ACD solution of CPD solution as an anticoagulant solution, the concentrations of glycerin and mannitol in the blood preserving solution of the present invention will be explained.

ACD solution (formula A) is an aqueous solution containing 0.8 g of citric acid, 2.2 g of sodium citrate and 2.2 g of glucose per 100 ml of the solution. Usually 30 ml of ACD solution is added to 200 ml of blood to be preserved.

CPD solution has a better buffer effect against pH change than ACD solution. CPD solution makes it possible to maintain the functions of erythrocytes in a higher level for a longer period of perservation than ACD solution. CPD solution is an aqueous solution containing 0.327 g of citric acid, 2.63 g of sodium citrate, 2.32 g of glucose and 0.251 g of sodium dihydrogenphosphate per 100 ml of the solution. Usually 28 ml of CPD solution is added to 200 ml of blood to be preserved.

Accordingly, to ACD solution were usually added glycerin in an amount of 3.3 to 10.0 w/v % and mannitol in an amount of 0.67 to 6.7 w/v %, preferably 0.67 to 3.3 w/v %. To CPD solution were usually added glycerin in an amount of 3.6 to 10.7 w/v % and mannitol in an amount of 0.71 to 7.1 w/v %, preferably 0.71 to 3.6 w/v %.

The blood preserving method of the present invention is characterized in that blood is preserved at a low temperature equal to or higher than the freezing temperature of the plasma by using the blood preserving solution of the present invention. A temperature lower than $5°\pm 1°$ C. which is a conventional preserving temperature is sufficient as the preserving temperature. However, a lower temperature near the freezing temperature of plasma (about $-1°$ C.) is desirable. From this point of view, a preferable temprature range is from the freezing temperature of plasma to 3° C.

A gas-permeable container is preferable as the blood preservation container used in the present invention. The use of a gas-permeable container as the blood preservation container is effective for maintaining the functions of erythrocytes, because carbon dioxide accumulated during preservation is removed by diffusion through the wall of the container so that the lowering of pH of the preserved blood is reduced to give a better environment for the erythrocyte metabolism.

With respect to the material of the preservation container, a bag-like container made of a soft synthetic resin such as soft vinyl chloride resins is better than a glass container, because the preservation in the former shows a smaller lowering of the functions of erythrocytes than that in the latter and has a practical advantage that treatments such as separation of blood components can be conducted under sterile conditions.

The present invention is applicable to the preservation of a blood preparation, particularly whole blood or packed blood cells.

The present invention is more specifically described and explained by means of the following Examples. It is to be understood that the present invention is not limited to the Examples, and various change and modifications may be made in the invention without departing from the spirit and scope thereof.

TEST EXAMPLE 1

To 200 ml of blood (whole blood) was added 28 ml of a conventional CPD solution. The blood mixed with CPD solution was preserved in a blood preservation bag made of a soft vinyl chloride resin at 4° to 6° C. which was the preserving temperature range conventionally adopted, or at 0° to 2° C. which was lower than the conventional preserving temperature by 4° C. The concentration of $Na^+$ in the plasma, concentration of $K^+$ in the plasma, the concentration of free hemoglobin, the concentration of 2,3-diphosphoglycerate (hereinafter referred to as 2,3-DPG) and adenosine triphosphate (hereinafter referred to as ATP) before the start of preservation and those 21 days after the start of preservation were determined. The results are shown in Table 1.

From the results shown in Table 1, it is clear that the effect of preservation depends upon the preserving temperature. That is, with respect to the items of plasma $Na^+$, plasma $K^+$ and free hemoglobin, the preservation at 4° to 6° C. is favorable. With respect to the items of 2,3-DPG and ATP which condition the effect and life of the preserved blood after transfusion, the preservation at 0° to 2° C. is favorable. These results show that, if blood can be preserved at a temperature lower than the conventional preserving temperature (4° to 6° C.), the blood preservation period for which a period of 3 weeks is conventionally provided can be still more extended and blood in a better state of preservation for transfusion can be provided. If it understood that in order to accomplish these objects, it is necessary to suppress the change of the electrolyte concentrations in the plasma and the hemolysis during the preservation.

As described above, the preservation at 4° to 6° C. is more favorable than the preservation at 0° to 2° C. with respect to the items of plasma $Na^+$, plasma $K^+$ and free hemoglobin. However, the concentrations of plasma $Na^+$, plasma $K^+$ and free hemoglobin after the preservation at 4° to 6° C. greatly deviate from the respective normal ranges (i.e. plasma $Na^+$: 135 to 145 mEq/l, plasma $K^+$: 3.5 to 4.5 mEq/l, free hemoglobin: 0 to 20 mg/dl).

TABLE 1

|  | Initial | After 21 days | |
| --- | --- | --- | --- |
|  |  | 0° to 2° C. | 4° to 6° C. |
| Plasma $Na^+$ (mEq/l) | 147.6 ± 1.6 | 127.1 ± 4.7 | 130.2 ± 2.9 |
| Plasma $K^+$ (mEq/l) | 2.9 ± 0.2 | 25.4 ± 3.4 | 18.9 ± 1.9 |
| Free hemoglobin (mg/dl) | 2.2 ± 2.8 | 66.5 ± 23.7 | 33.1 ± 13.5 |
| 2,3-DPG ($\mu$mol/mlRBC) | 4.36 ± 0.45 | 1.31 ± 0.62 | 0.38 ± 0.17 |
| ATP ($\mu$mol/mlRBC) | 1.14 ± 0.19 | 0.79 ± 0.18 | 0.66 ± 0.20 |

Note:
The concentrations of plasma $Na^+$ and $K^+$ were determined by use of ion-selective electrodes.
RBC means red blood cells.

TEST EXAMPLE 2

To 200 ml of whole blood were added 28 ml of CPD solution and glycerin in an amount of 1.5 w/v %, 2.0 w/v %, 3.0 w/v % or 0 w/v % on the basis of the amount of blood. Each blood sample was preserved in the same kind of preservation container as used in Test Example 1. With respect to each sample after preserved for 21 days, the concentrations of plasma $Na^+$, plasma $K^+$ and free hemoglobin were determined. The results are shown in Table 2.

The results reveal that the effect of glycerin is sufficiently exhibited in a concentration which is from 1/10 to 1/30 time the glycerin concentration used in freezing preservation and it is not enhanced any more in a concentration higher than about 2 w/v %.

However, from a separate test, it is known that the glycerin-containing blood preserved in the above manner is not suitable as a preserved blood for transfusion, since hemolysis occurs when it is suspended into a physiological saline solution.

Further, the glycerin used in a depression treatment for cerebral edema is used in the form of a solution wherein glycerin and fructose are dissolved in a physiological saline solution in concentrations of 10% and 5%, respectively. The purpose of adding fructose is to prevent the hemolysis which occurs when glycerin is infused by means of an intravenous drip. However, from the experiments wherein the preservation of blood is conducted in various concentrations of fructose and glycerin, it is known that the effect of fructose cannot be expected for the preservation of blood.

TABLE 2

| Glycerin (w/v %) | Plasma $Na^+$ (mEq/l) | Plasma $K^+$ (mEq/l) | Free hemoglobin (mg/dl) |
| --- | --- | --- | --- |
| 1.5 | 136.6 | 16.9 | 12.1 |
| 2.0 | 138.8 | 14.3 | 10.6 |
| 3.0 | 145.2 | 13.1 | 9.4 |
| 0 | 126.4 | 24.4 | 18.3 |

TEST EXAMPLE 3

This test example was conducted for the purposes of investigating the mechanism of the hemolysis of the preserved glycerin-containing blood which occurred when the preserved blood was suspended in a physiological saline solution and of finding a means for suppressing the sudden change of the osmotic pressure difference between the blood cell and the plasma to prevent the hemolysis.

To 200 ml of whole blood were added 28 ml of CPD solution, glycerin in the concentration shown in Table 3 and mannitol in the concentration shown in Table 3. Each blood sample was preserved in the same kind of container as used in Test Example 1 at 0° to 2° C. for 21 days. After the preservation, the concentrations of plasma $Na^+$, plasma $K^+$ and free hemoglobin were determined. Further hemolysis rate was determined. The hemolysis rate is defined as follows:

$$\text{Hemolysis rate (\%)} = \frac{\left(\begin{array}{c}\text{The amount of free} \\ \text{hemoglobin formed when} \\ \text{50 }\mu\text{l of blood is added} \\ \text{to 3 ml of a physiological} \\ \text{saline solution}\end{array}\right)}{\left(\begin{array}{c}\text{The amount of free} \\ \text{hemoglobin formed when} \\ \text{50 }\mu\text{l of blood is added} \\ \text{to 3 ml of water}\end{array}\right)} \times 100$$

The results are shown in Table 3.

The results reveal that by the addition of mannitol, the hemolysis can be prevented but the changes of the electrolyte concentrations in plasma cannot be suppressed, and accordingly the combination use of glycerin and mannitol is essential.

It is concluded that the combination use of glycerin in a concentration of 0.5 to 1.5 w/v % and mannitol in a concentration of 0.1 to 1.0 w/v %, especially 0.1 to 0.5 w/v % gives good results.

TABLE 3

| Concentration of glycerin (w/v %) | Concentration of mannitol (w/v %) | Plasma $Na^+$ (mEq/l) | Plasma $K^+$ (mEq/l) | Free hemoglobin (mg/dl) | Hemolysis rate (%) |
| --- | --- | --- | --- | --- | --- |
| 2.0 | 1.0 | 119.8 | 25.1 | 24.4 | 1.8 |
| 2.0 | 0.5 | 126.5 | 24.8 | 19.9 | 3.5 |
| 2.0 | 0.25 | 129.9 | 24.4 | 22.6 | 4.7 |
| 2.0 | 0 | 135.5 | 24.0 | 33.5 | 15.5 |
| 1.5 | 1.0 | 118.7 | 25.8 | 23.5 | 0.7 |
| 1.5 | 0.5 | 125.4 | 24.8 | 25.0 | 1.9 |
| 1.5 | 0.25 | 128.8 | 24.8 | 26.3 | 2.4 |
| 1.5 | 0 | 135.8 | 22.1 | 29.3 | 4.2 |
| 1.0 | 1.0 | 119.2 | 25.7 | 21.9 | 0.4 |

TABLE 3-continued

| Concentration of glycerin (w/v %) | Concentration of mannitol (w/v %) | Plasma Na+ (mEq/l) | Plasma K+ (mEq/l) | Free hemoglobin (mg/dl) | Hemolysis rate (%) |
|---|---|---|---|---|---|
| 1.0 | 0.5 | 127.8 | 25.3 | 23.7 | 0.5 |
| 1.0 | 0.25 | 130.9 | 25.0 | 16.5 | 0.6 |
| 1.0 | 0 | 132.0 | 24.9 | 30.1 | 1.5 |
| 0.5 | 1.0 | 121.1 | 26.8 | 20.1 | 0.3 |
| 0.5 | 0.5 | 125.7 | 26.8 | 20.2 | 0.2 |
| 0.5 | 0.25 | 128.7 | 26.8 | 21.8 | 0.3 |
| 0.5 | 0 | 128.8 | 27.6 | 32.6 | 0.3 |
| 0.25 | 1.0 | 120.2 | 27.5 | 22.5 | 0.2 |
| 0.25 | 0.5 | 125.2 | 28.7 | 23.8 | 0.2 |
| 0.25 | 0.25 | 126.2 | 29.3 | 23.6 | 0.2 |
| 0.25 | 0 | 129.5 | 30.6 | 35.2 | 0.2 |
| 0 | 0 | 124.1 | 30.9 | 56.4 | 0.8 |

TEST EXAMPLE 4

Four hundred ml of whole blood collected was divided into two groups (each group: 200 ml).

To 200 ml of the first group of the blood were added 28 ml of CPD solution, and glycerin and mannitol in amounts of 1.0 w/v % and 0.25 w/v %, respectively, on the basis of the amount of the blood (Invention A). The blood was preserved in the same kind of container as used in Test Example 1 at 1°±1° C. for 4 weeks. Various characteristics were measured. The results are shown in Table 4.

For comprison, the second group of the blood mixed with only CPD solution was preserved at 1°±1° C. for 4 weeks (Control). The results thereof are also shown in Table 4.

TABLE 4

| | Blood immediately after collected | Preservation at 1° ± 1° C. for 4 weeks | |
|---|---|---|---|
| | | Control | Invention A |
| pH | 6.996 ± 0.041 | 6.562 ± 0.037 | 6.536 ± 0.035 |
| Pco2 (mmHg) | 77.2 ± 11.2 | 123.5 ± 6.8 | 121.5 ± 6.7 |
| Na+ (mEq/l) | 149.0 ± 0.9 | 126.7 ± 2.5 | 128.3 ± 2.7 |
| K+ (mEq/l) | 2.8 ± 0.1 | 27.4 ± 2.5 | 24.1 ± 2.3 |
| Glucose (mg/dl) | 354.6 ± 30.1 | 236.1 ± 16.3 | 222.1 ± 20.6 |
| 2,3-DPG (μmol/mlRBC) | 4.05 ± 0.33 | 0.74 ± 0.22 | 0.62 ± 0.08 |
| ATP (μmol/mlRBC) | 1125 ± 121 | 718 ± 96 | 695 ± 116 |
| Free hemoglobin (mg/dl) | 2.6 ± 0.9 | 50.0 ± 25.4 | 38.6 ± 17.0 |

TEST EXAMPLE 5

Three hundred ml of whole blood collected was divided into three groups(each group: 100 ml).

To 100 ml of the first group of the blood were added 14 ml of CPD solution, and glycerin and mannitol in amounts of 0.5 w/v % and 0.25 w/v, respectively, on the basis of the amount of the blood. The blood was preserved in the same kind of container as used in Test Example 1 at 1°±1° C. for 4 weeks (Invention B). The second group of the blood mixed with CPD solution, glycerin and mannitol in the same manner as in the above was preserved in a gas-permeable container made of silicone laminated polyethylene film at 1°±1° C. for 4 weeks (Invention C). Various characteristics were measured. The results are shown in Table 5.

For comparison, the third group of the blood mixed with only CPD solution (Control) was preserved in the same manner as in Invention B. The results are also shown in Table 5.

TABLE 5

| | Blood immediately after collected | Control | Invention B | Invention C |
|---|---|---|---|---|
| pH | 7.003 ± 0.017 | 6.708 ± 0.027 | 6.680 ± 0.021 | 6.772 ± 0.042 |
| Pco2 (mmHg) | 68.7 ± 6.5 | 106.1 ± 7.0 | 106.3 ± 6.3 | 52.0 ± 5.7 |
| Na+ (mEq/l) | 144.8 ± 1.8 | 130.9 ± 2.5 | 132.3 ± 3.1 | 129.8 ± 2.5 |
| K+ (mEq/l) | 2.5 ± 0.1 | 28.2 ± 4.0 | 24.9 ± 3.9 | 26.2 ± 1.1 |
| Glucose (mg/dl) | 365.4 ± 13.8 | 228.3 ± 12.7 | 209.3 ± 11.6 | 191.0 ± 18.6 |
| 2,3-DPG (μmol/mlRBC) | 3.96 ± 0.21 | 0.81 ± 0.45 | 0.68 ± 0.18 | 0.98 ± 0.30 |
| ATP (μmol/mlRBC) | 1485 ± 108 | 960 ± 116 | 936 ± 98 | 1012 ± 178 |
| Free hemoglobin (mg/dl) | 1.3 ± 0.7 | 49.1 ± 17.3 | 41.5 ± 20.4 | 52.4 ± 21.5 |

TEST EXAMPLE 6

Blood samples each mixed with 28 ml of CPD solution, and glycerin and mannitol in the concentration shown in Table 6 per 200 ml of the blood were prepared.

TABLE 6

| Glycerin concentration (w/v %) | Mannitol concentration (w/v %) | | | |
|---|---|---|---|---|
| 0.25 | 0 | 0.25 | 0.5 | 1.0 |
| 0.5 | 0 | 0.25 | 0.5 | 1.0 |
| 1.0 | 0 | 0.25 | 0.5 | 1.0 |
| 1.5 | 0 | 0.25 | 0.5 | 1.0 |
| 2.0 | 0 | 0.25 | 0.5 | 1.0 |

Each blood sample was preserved in the same kind of container as used in Test Example 1 at 1°±1° C. for 3 weeks. With respect to glycerin and mannitol concentrations, the concentrations of plasma Na+, plasma K+ and free hemoglobin, and the hemolysis rate were determined. The results are shown in FIGS. 1 to 4.

FIG. 1: Concentration of plasma Na+
FIG. 2: Concentration of plasma K+
FIG. 3: Concentration of free hemoglobin
FIG. 4: Hemolysis rate A blood sample mixed with only CPD solution was preserved in the manner as above (Control). The results are also shown in FIGS. 1 to 4.

In addition to the ingredients used in the Examples, other ingredients can be used in the Examples as set forth in the specification to obtain substantially the same results.

As is clear from the above-mentioned, the blood preserving solution of the present invention suppresses the decrease in the concentration of $Na^+$ in the plasma, the increase in the concentration of $K^+$ in the plasma, the increase in the concentration of free hemoglobin due to hemolysis, and the use of the preserving solution makes it possible to preserve blood at a temperature lower than the conventional preserving temperature. According to the blood preserving method of the present invention, the period of preservation can be extended to 4 to 5 weeks with suppressing the hemolysis sufficiently, as compared to the conventional preserving method and the lowering of the functions of erythrocytes can be reduced. Accordingly, the wasting of valuable preserved blood can be reduced.

What is claimed is:

1. In a preserving solution for blood or packed blood cells comprising an anticoagulant solution containing citric acid, sodium citrate and glucose, the improvement comprising adding to said anticoagulant solution 0.5 to 1.5 w/v % of glycerin and 0.1 to 1.0 w/v % of mannitol, on the basis of the volume of blood or packed blood cells to be preserved.

2. The preserving solution of claim 1, wherein the concentration of mannitol is from 0.1 to 0.5 w/v % on the basis of the amount of the blood or packed blood cells to be preserved.

3. The preserving solution of claim 1, wherein the anticoagulant solution is CPD solution.

4. The preserving solution of claim 1, which further contains a material serving as an energic source for metabolism of hemocytes in blood or packed blood cells, and a material for maintaining the functions of erythrocytes which decrease with increasing period of preservation.

5. In a method for preserving blood or packed blood cells comprising adding to blood or packed blood cells a preserving solution comprising an anticoagulant solution containing citric acid, sodium citrate and glucose and storing the blood or packed blood cells at a low temperature, the improvement comprising adding to said anticoagulant solution 0.5 to 1.5 w/v % of glycerin and 0.1 to 1.0 w/v % of mannitol, on the basis of the volume of blood or packed blood cells to be preserved, and storing said blood or packed blood cells at a temperature between the freezing temperature of plasma and 3° C.

6. The method of claim 5, wherein the concentration of mannitol is from 0.1 to 0.5 w/v % on the basis of the amount of the blood or packed blood cells to be preserved.

7. The method of claim 5, wherein the anticoagulant solution is CPD solution.

8. The method of claim 5, wherein said preserving solution further contains a material serving as an energic source for metabolism of hemocytes in blood or packed blood cells, and a material for maintaining the functions of erythrocytes which decrease with increasing period of preservation.

9. The method of claim 5, wherein the storage temperature is from −1° to 3° C.

10. The method of claim 5, wherein the storage temperature is −1° to 1° C.

* * * * *